(12) United States Patent
Windolf et al.

(10) Patent No.: US 10,736,644 B2
(45) Date of Patent: Aug. 11, 2020

(54) SURGICAL POWER DRILL INCLUDING A MEASURING UNIT SUITABLE FOR BONE SCREW LENGTH DETERMINATION

(71) Applicant: Synthes GmbH, Zuchwil (CH)

(72) Inventors: Markus Windolf, Davos (CH); Michael Schuetz, St. Lucia (AU)

(73) Assignee: Synthes GmbH, Zuchwil (CH)

( * ) Notice: Subject to any disclaimer, the term of this patent is extended or adjusted under 35 U.S.C. 154(b) by 212 days.

(21) Appl. No.: 15/774,798

(22) PCT Filed: Nov. 11, 2016

(86) PCT No.: PCT/CH2016/000143
§ 371 (c)(1),
(2) Date: May 9, 2018

(87) PCT Pub. No.: WO2017/083992
PCT Pub. Date: May 26, 2017

(65) Prior Publication Data
US 2018/0325528 A1    Nov. 15, 2018

(30) Foreign Application Priority Data

Nov. 16, 2015 (WO) ................ PCT/CH2015/000168

(51) Int. Cl.
*A61B 17/16* (2006.01)
(52) U.S. Cl.
CPC ...... *A61B 17/1626* (2013.01); *A61B 17/1615* (2013.01); *A61B 17/1622* (2013.01); *A61B 17/1633* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS 1,831,813 A * 11/1931 Axel ................. B23B 49/02
408/81
2,883,891 A * 4/1959 Robinson ............ B25F 5/003
408/112
(Continued)

FOREIGN PATENT DOCUMENTS

WO    2015006296 A1    1/2015
WO    2015106304 A1    7/2015

*Primary Examiner* — Eric S Gibson
(74) *Attorney, Agent, or Firm* — BakerHostetler

(57) ABSTRACT

A device (25) for drilling holes in bone and configured to determine bone screw length, the device (25) including a surgical power drill (2) comprising: a) a housing (12) and; b) a measuring device (1) releasably attached or fixed to the housing (12), wherein the measuring device (1) is configured to measure the distance (x) covered by the housing (12) in the direction of the longitudinal axis (7) and relative to a surface of an implant (26) or a bone during a drilling process, wherein the measuring device (1) comprises a processing unit (14) to record the distance (x) covered with respect to time; the processing unit (14) comprises one or more differentiators to determine at least the first and second derivatives of the distance (x) covered with respect to time; and the processing unit (14) further comprises a peak detector to analyze one or more peaks occurring in the graph of the highest derivative with respect to time, and wherein the measuring device (1) comprises a laser device or an ultrasound position sensor for displacement assessment.

23 Claims, 10 Drawing Sheets

(58) Field of Classification Search
CPC ............ A61B 17/1624; A61B 17/1626; A61B 17/1628
See application file for complete search history.

(56) References Cited

U.S. PATENT DOCUMENTS

| | | | | | |
|---|---|---|---|---|---|
| 4,157,231 | A * | 6/1979 | Phillips | ................ | E21B 19/086 408/1 R |
| 4,310,269 | A * | 1/1982 | Neu | ................ | B23B 47/32 408/10 |
| 4,329,092 | A * | 5/1982 | Ponitzsch | ................ | B23B 45/04 408/10 |
| 4,329,095 | A * | 5/1982 | Schmuck | ................ | B23B 49/006 408/112 |
| 4,644,335 | A * | 2/1987 | Wen | ................ | G01H 1/003 340/680 |
| 5,014,793 | A * | 5/1991 | Germanton | ................ | B25B 21/00 173/181 |
| 5,071,293 | A * | 12/1991 | Wells | ................ | B23B 49/02 408/112 |
| 5,411,503 | A * | 5/1995 | Hollstien | ................ | A61B 17/1707 606/80 |
| 5,533,842 | A * | 7/1996 | Johnson | ................ | B23Q 5/265 408/130 |
| 5,538,423 | A * | 7/1996 | Coss | ................ | A61C 1/0015 408/8 |
| 5,584,838 | A * | 12/1996 | Rona | ................ | A61B 17/1707 324/226 |
| 5,599,142 | A * | 2/1997 | Fujimoto | ................ | B23Q 15/12 408/10 |
| 5,613,810 | A * | 3/1997 | Bureller | ................ | B23Q 15/12 408/11 |
| 5,810,828 | A * | 9/1998 | Lightman | ................ | A61B 17/164 606/80 |
| 5,961,257 | A * | 10/1999 | Bettini | ................ | E01B 31/24 408/97 |
| 5,980,248 | A * | 11/1999 | Kusakabe | ................ | A61C 1/0007 433/131 |
| 6,033,409 | A * | 3/2000 | Allotta | ................ | A61B 17/1622 606/170 |
| 6,096,042 | A * | 8/2000 | Herbert | ................ | B23B 49/006 606/80 |
| 6,494,590 | B1 * | 12/2002 | Paganini | ................ | B25F 5/021 362/109 |
| 6,527,778 | B2 * | 3/2003 | Athanasiou | ................ | A61B 10/0233 606/80 |
| 6,665,948 | B1 * | 12/2003 | Kozin | ................ | A61B 17/1626 175/45 |
| 6,786,683 | B2 * | 9/2004 | Schaer | ................ | B23B 49/006 408/16 |
| 6,925,725 | B2 * | 8/2005 | Herrmann | ................ | B21J 15/10 33/638 |
| 7,073,989 | B2 * | 7/2006 | Erickson | ................ | B23B 45/003 408/112 |
| 7,185,998 | B2 * | 3/2007 | Oomori | ................ | B25B 23/18 362/119 |
| 7,235,940 | B2 * | 6/2007 | Bosch | ................ | B25B 23/147 173/4 |
| 7,482,819 | B2 * | 1/2009 | Wuersch | ................ | B23B 49/006 173/6 |
| 7,578,642 | B2 * | 8/2009 | Fritsche | ................ | B23Q 1/28 227/110 |
| 7,681,659 | B2 * | 3/2010 | Zhang | ................ | B23D 59/001 173/1 |
| 7,946,049 | B1 * | 5/2011 | Wilton | ................ | B25F 5/02 33/526 |
| 7,992,311 | B2 * | 8/2011 | Cerwin | ................ | G01C 15/002 33/286 |
| 8,162,074 | B2 * | 4/2012 | Cook | ................ | B23B 45/001 16/114.1 |
| 8,167,518 | B2 * | 5/2012 | Mathis | ................ | B23Q 5/225 408/1 R |
| 8,171,642 | B2 * | 5/2012 | Fritsche | ................ | B23Q 1/28 29/283 |
| 8,317,437 | B2 * | 11/2012 | Merkley | ................ | B23B 35/00 408/12 |
| 8,734,153 | B2 * | 5/2014 | Arzanpour | ................ | A61C 1/0007 433/114 |
| 8,821,493 | B2 * | 9/2014 | Anderson | ................ | A61B 17/1624 606/80 |
| 8,894,654 | B2 * | 11/2014 | Anderson | ................ | A61B 17/1626 606/80 |
| 8,925,169 | B2 * | 1/2015 | Schevers | ................ | B23B 49/00 29/407.08 |
| 8,970,207 | B2 * | 3/2015 | Baumgartner | ................ | G01D 5/145 324/207.2 |
| 9,114,494 | B1 * | 8/2015 | Mah | ................ | B23Q 17/2233 |
| 9,204,885 | B2 * | 12/2015 | McGinley | ................ | A61B 17/142 |
| 9,358,016 | B2 * | 6/2016 | McGinley | ................ | A61B 90/30 |
| 9,370,372 | B2 * | 6/2016 | McGinley | ................ | A61B 90/30 |
| 9,492,181 | B2 * | 11/2016 | McGinley | ................ | A61B 17/1626 |
| 2001/0047219 | A1 * | 11/2001 | Oden | ................ | B23Q 17/12 700/159 |
| 2003/0049082 | A1 * | 3/2003 | Morrison | ................ | B23B 49/026 408/56 |
| 2004/0146367 | A1 * | 7/2004 | Gerhardt | ................ | B25F 5/003 408/110 |
| 2004/0179829 | A1 * | 9/2004 | Phillips | ................ | H02P 29/02 388/804 |
| 2004/0215395 | A1 * | 10/2004 | Strasser | ................ | B23B 49/006 702/9 |
| 2005/0116673 | A1 * | 6/2005 | Carl | ................ | A61B 17/1626 318/432 |
| 2005/0131415 | A1 * | 6/2005 | Hearn | ................ | A61B 17/1626 606/80 |
| 2005/0169717 | A1 * | 8/2005 | Field | ................ | B23B 49/00 408/13 |
| 2005/0261870 | A1 * | 11/2005 | Cramer | ................ | B23B 49/008 702/166 |
| 2006/0008771 | A1 * | 1/2006 | Courvoisier | ................ | A61B 17/16 433/165 |
| 2007/0030486 | A1 * | 2/2007 | Gelbart | ................ | B23Q 17/2233 356/399 |
| 2007/0035311 | A1 * | 2/2007 | Wuersch | ................ | B23B 49/006 324/644 |
| 2009/0245956 | A1 * | 10/2009 | Apkarian | ................ | A61B 17/1626 408/1 R |
| 2009/0299439 | A1 * | 12/2009 | Mire | ................ | A61B 17/1626 607/60 |
| 2009/0326537 | A1 * | 12/2009 | Anderson | ................ | A61B 90/06 606/80 |
| 2010/0137874 | A1 * | 6/2010 | Kim | ................ | G01B 3/28 606/102 |
| 2011/0020084 | A1 | 1/2011 | Brett et al. | | |
| 2011/0060242 | A1 * | 3/2011 | Hausman | ................ | A61B 17/1626 600/554 |
| 2011/0245833 | A1 * | 10/2011 | Anderson | ................ | A61B 17/1626 606/80 |
| 2011/0301611 | A1 * | 12/2011 | Garcia | ................ | A61B 17/162 606/80 |
| 2012/0037386 | A1 * | 2/2012 | Cook | ................ | B23B 45/001 173/30 |
| 2013/0189041 | A1 | 7/2013 | Abe et al. | | |
| 2013/0304069 | A1 * | 11/2013 | Bono | ................ | A61B 17/1624 606/80 |
| 2013/0307529 | A1 * | 11/2013 | Baumgartner | ................ | G01D 5/145 324/207.2 |
| 2014/0107471 | A1 * | 4/2014 | Haider | ................ | A61B 17/1703 600/424 |
| 2014/0148808 | A1 | 5/2014 | Inkpen et al. | | |
| 2015/0066030 | A1 * | 3/2015 | McGinley | ................ | A61B 17/142 606/79 |
| 2015/0066035 | A1 * | 3/2015 | McGinley | ................ | A61B 17/16 606/80 |
| 2015/0066036 | A1 * | 3/2015 | McGinley | ................ | A61B 17/1615 606/80 |
| 2015/0066037 | A1 * | 3/2015 | McGinley | ................ | A61B 17/16 606/80 |

(56) References Cited

U.S. PATENT DOCUMENTS

2015/0066038 A1* 3/2015 McGinley .......... A61B 17/1626
606/80
2015/0165580 A1* 6/2015 Holland ............. B23Q 17/2275
408/1 BD
2018/0325528 A1* 11/2018 Windolf ............. A61B 17/1622

* cited by examiner

SURGICAL POWER DRILL INCLUDING A MEASURING UNIT SUITABLE FOR BONE SCREW LENGTH DETERMINATION

BACKGROUND OF THE INVENTION

1. Field of the Invention

The invention relates to a surgical power drill including a measuring unit suitable for bone screw length determination according to the preamble of independent claim 1, to a device including a surgical power drill and a measuring unit suitable for bone screw length determination according to the preamble of independent claim 2 and to a method for bone screw length estimation from drilling characteristics using the surgical power drill.

From clinical observations one problem in orthopedic and trauma surgery is the determination of the required screw lengths for e.g. bi-cortical screw placement before inserting a screw into a bone fragment. Current mechanical depths gauges are rather inaccurate, unreliable and difficult to handle resulting in:
- prolonged surgery time;
- insertion of too long screws resulting in soft tissue irritation, pain and re-operation;
- insertion of too short screws resulting in osteosynthesis failure, re-operation;
- need for exchange of screws resulting in screw scrap, increased hardware costs.

2. Description of the Related Art

WO 2015/006296 XIE

A surgical drill having an integrated depth measuring device is known from WO 2015/006296 XIE. This known surgical drill comprises a telescoping rod with a sleeve which slides along the drill bit during operation and the distal end of which abuts on the proximal surface of a bone, a brake mechanism suitable to stop movement of the telescoping rod relative to the drill bit and an actuator to engage the brake mechanism in response to a command signal indicating when the drill bit penetrates through bone. A sensor measures the electrical current drawn by the motor of the drill device. When the drill bit bores through the distal side of the bone, the frictional force generated by the drill bit rubbing against the bone suddenly decreases resulting in a rapid decrease of the electrical current drawn by motor. The sudden drop in the current drawn by the motor over a time period is measured or sensed by a sensor and a processor, which is executing a braking module software, comparing the change in electrical current data received from the sensor to a pre-determined threshold change in current or current drop level that is stored in sensor parameter threshold values. The length of the drill bit that extends beyond the distal end of the sleeve is measured by means of a scale or depth gauge affixed to the telescoping rod. Alternatively, the length of the drill bit that extends beyond the distal end of the sleeve is measured by means of a digital caliper. A drawback of this known surgical drill is that it includes two different measuring devices, a first one for detecting when the drill bit exits a bone by measurement of the electric current drawn by the motor and a second one for determining the drilling depth resulting in a complex electrical and mechanical measuring system.

A further surgical power drill including an integrated depth measuring device is known from US 2015/066030 MCGINGLEY ET AL. This known surgical power drill comprises a measuring device configured as a linear variable differential displacement transducer (LVDT) attached to the housing, wherein the measuring device is configured to measure the distance x covered by the housing in the direction of the longitudinal axis and relative to a surface of a bone during a drilling process. The measuring device comprises a processing unit including one or more differentiators to determine the first and second time derivative of the distance x covered with respect to time. Furthermore, the measuring device includes an additional sensor to measure the force applied to the drill bit and the use of a third signal indicating the instant of time when the drill bit exits a bone cortex, wherein the third signal is output when the second time derivative (acceleration) of the first signal (displacement) is greater than zero and the first time derivative of the second signal (force applied to the drill bit) is less than zero. A drawback of this known surgical power drill is that due to the rod connecting the displaceable tip to the sensor of the measuring device the measuring device has an unwieldy configuration resulting in a cumbersome handling for the surgeon. Furthermore, the rod impedes the view of the surgeon on the operation site.

BRIEF SUMMARY OF THE INVENTION

It is an object of the invention to provide a surgical power drill comprising a measuring device which has a simple configuration and permits bone screw length estimation based on drilling characteristics only.

The invention solves the posed problem with a surgical power drill including a measuring unit suitable for bone screw length determination comprising the features of claim 1, with a device including a surgical power drill and a measuring unit suitable for bone screw length determination comprising the features of claim 2 and with a method for bone screw length estimation from drilling characteristics using the surgical power drill.

The advantages of the surgical power drill can essentially be seen therein that:
- the configuration of the measuring device with a use of a laser device or an ultrasound position sensor for displacement assessment by means of triangulation permits a simple configuration of the measuring device without a mechanical arm between the displaceable member and the sensor. Thereby the work field of the surgeon is not occupied nor is the field of view obstructed. Contactless distance measurement reduces the contamination risk of the patient and does not influence the drilling process as opposed to mechanical contact measurement. Furthermore, a significantly larger measuring range is achieved, e.g. 15 cm-30 cm compared to 6.4 cm of the known devices so that a large variety of drill bits and drill sleeves with different lengths can be used;
- due to the use of a sole position sensor and a processing unit that records the distance x covered by the housing relative to the surface of a bone or of an implant with respect to time during a drilling process and the use of one or more differentiators and a peak detector the measuring unit has a simple configuration and can hence be configured as a separate unit which can be temporarily attached to a standard surgical drilling machine.

Further advantageous embodiments of the invention can be commented as follows:

In a special embodiment the processing unit is one of a computer with monitor, a tablet computer, a smartphone, a smartwatch or a smartglass, wherein the processing unit is suitably programmed to compute the at least first and second derivatives of the distance x covered with respect to time so as to form at least a first and a second differentiator and wherein the processing unit is suitably programmed to form a peak detector.

In a further embodiment the peak detector is configured to identify an acceleration peak when the maximum value of the determined acceleration exceeds a pre-defined threshold value.

Therewith the advantage can be achieved that the threshold value permits to reliably detect the position x where the cutting tip of the drill bit exits the cortex of a bone. The processing unit can report two values for the position where the peak value of the highest derivative exceeds the threshold value which occurs at the positions where the cutting tip of the drill bit exits the near cortex, respectively the far cortex of a bone. The surgeon can then decide whether unicortical or bicortical bone screws are to be applied.

In again a further embodiment the processing unit comprises a third differentiator to determine the third derivative of the distance x covered by the housing in the direction of the longitudinal axis and relative to a surface of an implant or a bone with respect to time during a drilling process. The third derivative of the position x with respect to time, respectively the first derivative of the acceleration vs. time or the second derivative of the velocity vs. time is the so called jerk. The jerk peaks are more distinct than the acceleration peaks so that the significance of the detection of the point where the drill bit exits the cortex of a bone can be improved. Furthermore, the jerk peaks are located closer to the exit points than the acceleration peaks.

In another embodiment the peak detector is configured to identify a jerk peak when the maximum value of the determined jerk exceeds a pre-defined threshold value for the jerk.

In a further embodiment the processing unit comprises a microprocessor or a central processing unit having a processor register to record the distance x covered by the housing in the direction of the longitudinal axis and relative to a surface of an implant or a bone with respect to time during a drilling process, wherein the microprocessor or central processing unit is suitably programmed to compute the at least first and second derivatives of the distance x covered by the housing in the direction of the longitudinal axis and relative to a surface of an implant or a bone with respect to time so as to form at least a first and a second differentiator and wherein the microprocessor or central processing unit is suitably programmed to form a peak detector. The peak occurring when the drill bit exits the cortex can be clearly distinguished from the peaks occurring when the drill bit enters the cortex from displacement of the drill bit while drilling.

In a further embodiment the processor register of the microprocessor or central processing unit temporarily stores acceleration and/or jerk peak values determined during a drilling process to define threshold values for acceleration and/or jerk. By this means the advantage is achieved that the threshold values can be retrospectively set in relation to the maximum recorded peak under the assumption that the number of expected peaks is known (e.g. two peaks for the near and far cortex).

In another embodiment the microprocessor or central processing unit is programmed to compute the derivatives, to detect the peaks and to output the current distance x and/or the current velocity in real-time.

In yet another embodiment the measuring device comprises attachment means, preferably an adaptor which is releasably affixable to the housing of the surgical power drill. This configuration permits the advantage that the measuring device can be configured as a separate unit which can be temporarily attached to a standard surgical power drill.

In a further embodiment the measuring device comprises clamps to releasably affix the measuring device to the housing.

In further embodiment the adaptor is configured as a framework attachable to the housing, preferably an annular framework to be secured to the housing by means of a press fit or via a clamp collar.

In another embodiment the measuring device comprises a wireless data transmission device, preferably a Bluetooth module with a signal conditioner. The derived information, i.e. the measured position x of the cutting tip of the drill bit with respect to time as well as the computed velocity and acceleration with respect to time and the computed jerk with respect to time may be transmitted wirelessly to an external device such as a computer with monitor, a tablet computer, a smartphone, a smartwatch or a smartglass.

In another embodiment the measuring device comprises a casing to enclose the processing unit and preferably the wireless communication device.

Preferably, the casing enclosing the processing unit is sterilizable.

In another embodiment the measuring devices comprises a power supply, preferably one or more rechargeable or non-rechargeable batteries arrangeable in the casing or arrangeable in the housing to additionally supply electric power to the electric motor of the surgical power drill.

In again a further embodiment the measuring device comprises: a first member, which is in a fixed position relative to the housing; and a longitudinal second member, which is displaceable essentially in the direction of the longitudinal axis of the spindle relative to the first member and which comprises a front end suitable to abut a surface of a bone or an implant.

In another embodiment the laser device comprises a laser module and at least two electronic light sensors, preferably charge-coupled devices (CCD) to perform laser triangulation for displacement assessment.

In again another embodiment the laser device comprises a reflector slideable along a drill bit and configured to abut an implant, a bone or an instrument.

In a further embodiment the displaceable second member of the measuring device comprises a sensing tip arranged at the front end of the second member and configured to abut an implant, a surface of a bone or an instrument.

In a further embodiment the processing unit comprises a data memory to store data related to bone screw lengths, preferably including a safety margin, screw head length, tip section length and screw length increments.

In again a further embodiment the measuring device additionally comprises a display or a loud speaker. The derived information may be provided on a display or speaker locally mounted to the drilling machine, wherein the main output parameters are:
  the current position x of the cutting tip of the drill bit which coincides with the measured distance x covered by the housing in the direction of the longitudinal axis and relative to the surface of the implant, the instrument or the bone;
  the current velocity of the forward moving drill bit; and the position of the cutting tip of the drill bit at the most recent jerk and/or acceleration peak, wherefrom the suitable implant length can be derived.

In another embodiment the device additionally comprises a calibration device.

In yet another embodiment the displaceable second member comprises a drill sleeve extending in the direction of the longitudinal axis to the front end of the second member. In a further embodiment the first member of the measuring device comprises a display.

In another embodiment the first member of the measuring device is insertable into a hollow space arranged in the housing of the surgical power drill.

Preferably, the first member is part of an electronic module which additionally comprises a power supply and/or a motor for driving the surgical power drill, wherein the power supply is configured to supply the first member and preferably the motor with electric energy.

Preferably, the hollow space is arranged in a handle of the housing and configured to receive the electronic module.

In a further embodiment the housing comprises a top part including a sterilizable window for covering the display.

In another embodiment the top part is integral with the housing and forms a casing for the display.

Preferably, the housing comprises at least one sterile window to provide a window for the laser beam emitted by the laser module and a reflected beam receivable by the electronic light sensor.

In another embodiment the processing unit is suitably programmed to control the rotational speed of the spindle of the surgical power drill.

In another embodiment the first member is part of an electronic module which additionally comprises a power supply for supplying the first member with electric energy.

In a further embodiment the casing is attachable to the housing by means of an adaptor and comprises a cavity configured to receive the electronic module.

Preferably, the casing comprises a lid arranged at the rear end of the casing and including a sterilizable rear window for covering the display.

Preferably, the casing comprises at least one sterile front window to provide a window for the laser beam emitted by the laser module and a reflected beam receivable by the electronic light sensor.

In another embodiment the measuring device is positioned with respect to the housing so that a laser beam emitted by the laser module is oriented at an offset angle to the longitudinal axis of the spindle. This configuration permits the advantage that the diameter of the displaceable second member can be reduced.

In another embodiment the first member of the measuring device is positioned off-center to the longitudinal axis of the spindle. Therewith the advantage can be achieved that the laser beams (emitted and reflected) are not obstructed by the drill-bit. The view of the operator is less obstructed.

In a further embodiment the measuring device comprises at least one push button with a sterile, flexible cover.

In a further embodiment the casing is transparent.

In again a further embodiment the casing is configured as a funnel to facilitate insertion of the electronic module into the cavity.

In another embodiment the displaceable second member comprises a clamping portion for attachment to cylindrical structures with variable diameters.

Preferably, the clamping portion of the displaceable second member is configured to provide a frictional fit to a drill bit. By this means the advantage can be achieved that the reflector can slide along a drill bit but will not move due to gravity or small impacts. This way the reflector is pushed against a surface of an instrument or implant without the need to accurately fit the geometry of the instrument or implant.

In another embodiment the displaceable second member comprises a reflector having a reflecting surface and a rim or groove shaped and dimensioned to provide information or trigger events to the processing unit. This configuration permits the advantage that the depth or position of the rim or groove can be used to automatically select e.g. the screw module or trigger an event like the taring mode, i.e. when setting the reference position.

In another embodiment the displaceable second member is rotation symmetric so that the reflector can rotate with the drill bit.

In a further embodiment the device comprises a calibration device which can be broken away after use.

In a further embodiment the displaceable second member or the calibration device or the casing are made from a material with a melting temperature below typical autoclave operating temperatures. This configuration prevents reuse of reflectors to improve safety.

In another embodiment the measuring device comprises at least one accelerometer. By this means the device can be operated by gestures rather than buttons. Example: taring is only possible when oriented vertical (within limits) pointing downwards. Switching back to taring mode by orienting the drill vertical pointing upwards. Sleep mode and wake-up by device movement to safe energy.

In again another embodiment the measuring device additionally comprises at least one gyroscope and/or at least one magnetometer. This configuration permits the advantage that the absolute orientation of the drill can be tracked to control the drilling direction.

In a special embodiment the method comprises before step A) the following steps: positioning the surgical power drill relative to a bone so that the front end of the displaceable second member and the cutting tip of the drill bit abut a surface of a bone; and storing the relative position as start point (x=0) for the measurement of the position x of the cutting tip of the drill bit relative to a surface of a bone in the drilling direction with respect to time. In this case the second member comprises a drill sleeve extending in the direction of the longitudinal axis to the front end of the second member.

In another embodiment the method comprises before step A) the following steps: positioning the surgical power drill relative to a bone so that the front end of the displaceable second member abuts a drill sleeve inserted in the soft tissue covering a bone to be treated; adjusting the cutting tip of the drill bit secured in the chuck of the surgical power drill relative to the displaceable second member so that the cutting tip of the drill bit abuts a surface of a bone; and storing the relative position as start point (x=0) for the measurement of the position x of the cutting tip of the drill bit relative to a surface of a bone or of an implant in the drilling direction with respect to time. In this case a separate drill sleeve can be used.

In a further embodiment the method comprises before step A) the following steps: positioning the drill bit secured in the chuck relative to the displaceable second member by using a calibration device so that front end of the second member contacts a surface of the calibration device and the cutting tip of the drill bit abuts a stop protruding from the surface of the calibration device; storing the relative position as start point (x=0) for the measurement of the position x of the cutting tip of the drill bit relative to a surface of a bone or of an implant in the drilling direction with respect to time; and positioning the surgical power drill relative to an implant, so that the front end of the displaceable second member abuts a surface of the implant.

A BRIEF DESCRIPTION OF THE DRAWINGS

Several embodiments of the invention will be described in the following by way of example and with reference to the accompanying drawings in which.

DETAILED DESCRIPTION OF THE INVENTION

Definitions

Figure 1:
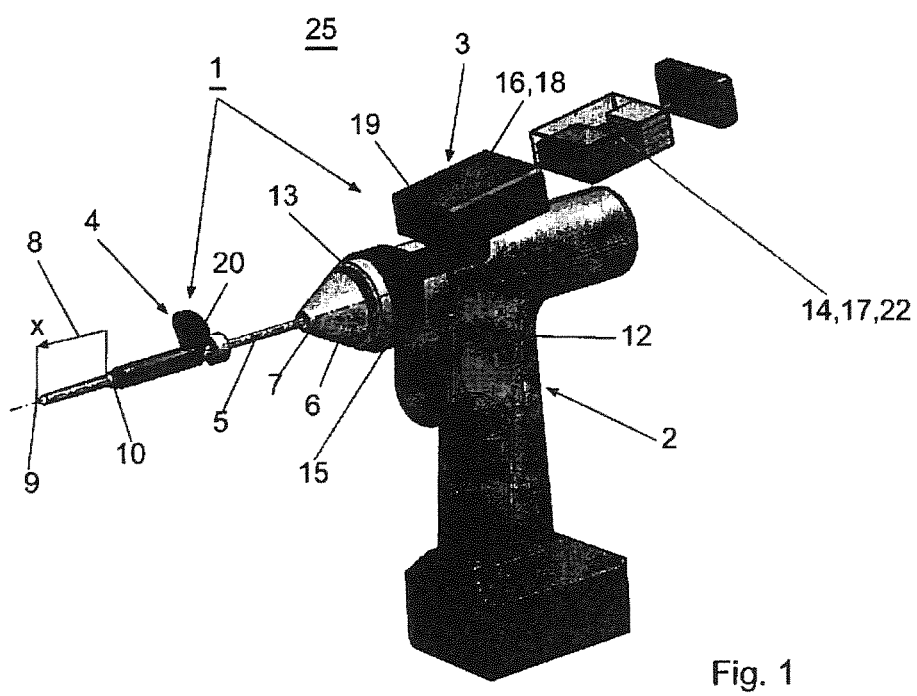
FIG. 1 illustrates a perspective view of an embodiment of the device according to the invention.

The following definitions of terms and wordings currently used describe the exact meaning thereof as they are used throughout the present specification:

Position x of the Cutting Tip of the Drill Bit Relative to a Surface of a Bone or of an Implant:

During a drilling process the distance x covered by the housing 12 in the direction of the longitudinal axis 7 of the spindle 13 and relative to a surface of a bone or of an implant 26 is related with the position x of the cutting tip 9 of the drill bit 5 relative to a surface of a bone or of an implant 26 in the drilling direction because the drill bit 5 is firmly fixed in the chuck 6 of the surgical power drill 2 and positioned at the beginning of the drilling process as described in detail below.

Differentiator:

The processing unit 14 of the device according to the invention can be configured by using digital technique or by using analog technique.

In the case that the processing unit 14 (FIGS. 1-4) is configured as a digital processing unit the processing unit 14 comprises a microprocessor or a central processing unit which is suitably programmed for performing a numerical differentiation of digitized signals, i.e. to compute the at least first and second derivatives of the relative position x between the cutting tip 9 of the drill bit 5 and the surface of a bone or of an implant 26 with respect to time during the drilling process (FIG. 1).

The numerical differentiation can exemplarily be performed by computing the average slope between two adjacent data points $[x'_i = (x_{i+1} - x_i)/\Delta t]$. Alternatively, an algorithm using three adjacent data points called central-difference method can be applied, wherein $[x'_i\ (x_{i+1} - x_{i-1})/2\Delta t]$. The latter method has the advantage that it does not involve a shift in the t-axis position of the derivative.

The measuring device 1 can comprise a signal conditioner to convert analog signals generated by a sensor into digitized signals. Furthermore, the processing unit 14 can be provided with a timer or a clock to record the relative position x with respect to time.

Alternatively, the processing unit 14 can be configured by using analog technique, e.g. electronic circuits including one or more electronic circuits acting as differentiators and an electronic circuit acting as a peak detector.

FIG. 1 illustrates an embodiment of the surgical power drill 2 according to the invention wherein the surgical power drill 2 essentially includes a housing 12 in which a motor and a spindle 13 driven by the motor are accommodated, a measuring device 1 releasably attached or fixed to the housing 12 and an adaptor 15 to secure the measuring device 1 to the housing 12. The spindle 13 has a longitudinal axis 7 and comprises a chuck 3 at a front end for clamping a drill bit 5. The measuring device 1 comprises a first member 3, which is in a fixed position relative to the housing 12 and a longitudinal second member 4, which is exemplarily but not limiting displaceable parallel or coaxial to the longitudinal axis 7 of the spindle 13 relative to the first member 3. Alternatively, the measuring device 1 can be arranged at the housing 12 so that the second member 4 is displaceable at an angle relative to the longitudinal axis 7 of the spindle 13. The systematic error which occurs due to this angulation (cosine error) can be easily compensated. This configuration has the advantage that the reflector can be smaller so that the measuring tip can be arranged closer to the drill bit 5.

The displaceable second member 4 has a front end 10, wherein in use the front end 10 of the displaceable second member 4 abuts the bone surface or a surface of an implant 26, e.g. a bone plate or a drill sleeve. The drill bit 5 can be clamped in the chuck 6 and is provided with a cutting tip 9. Furthermore, the displaceable second member 4 can comprise a drill sleeve 23 extending in the direction of the longitudinal axis 7 to the front end 10 of the second member 4.

The measuring device 1 comprises a laser device for linear displacement assessment. This laser device comprises a laser module 18 with a laser light emitting means, a reflector 20 attached to a drill sleeve 23 forming the second member 4 which is slideable along the drill bit 5 and at least two electronic light sensors 19, which are, exemplarily but not limiting, configured as charge-coupled devices (CCD) to perform laser triangulation for linear displacement assessment.

In another alternative embodiment the linear displacement assessment can be performed by using ultra sound position sensors.

To incorporate screw length determination in the drilling procedure so as to eliminate the step of depth measurement after drilling the hole in the bone the configuration of the measuring device 1 is based on the fact that during drilling an acceleration peak of the drill bit 5 occurs when the cutting tip 9 of the drill bit 5 exits a bone cortex as this is an unavoidable attribute of handheld drilling. Consequently, the housing 12 of the surgical power drill 2 together with the first member 3 of the measuring device 1 is subjected to the same acceleration.

Additionally, the processing unit 14 comprises one or more differentiators to determine at least the first and second derivatives of the position x with respect to time and a peak detector. The peak detector is applied to identify an acceleration and/or a jerk peak when the cutting tip 9 of the drill bit 5 exits the cortex of a bone. The graph of acceleration versus displacement, i.e. drilling depth is exemplarily illustrated in FIG. 5. The value of acceleration at the entry point (A) of the cutting tip 9 of the drill bit 5 is set to zero. A first peak of the acceleration occurs when the cutting tip 9 of the drill bit 5 exits the near cortex of a bone (8) and after an increase of the acceleration at the entry (C) of the cutting tip 9 of the drill bit 5 into the far cortex a second peak of the acceleration occurs when the cutting tip 9 of the drill bit 5 exits the far cortex of the bone (D). The first and second peak are clearly identifiable by a sudden distinct increase and a subsequent reversion of the acceleration specifying a clear and identifiable discontinuity in the acceleration versus displacement graph of the drill bit 5.

The measuring device 1 particularly measures and records the relative motion between the displaceable second member 4 and the first member 3 which is fixed with respect to the housing 12. Since the drill bit 5 is firmly clamped in the chuck 6 the relative motion between the displaceable second member 4 and the first member 3 coincides with the relative motion of the cutting tip 9 of the drill bit 5 with respect to the front end 10 of the displaceable second member 4. Therefore, the measuring device 1 measures and records the relative motion of the drill bit 5 in the drilling direction in real time with respect to the bone surface or to the surface of an implant on which the front end 10 of the displaceable second member 4 of the measuring device 1 abuts. The motion of the drill bit 5 relative to the displaceable second member 4 of the measuring device 1 is a one-dimensional translational motion and the position x of the cutting tip 9 of the drill bit 5 relative to the front end 10 of the displaceable second member 4 at any moment is given by the x coordinate of the cutting tip 9 along the x-axis 8 which in this case forms the reference frame. The position x or x coordinate of the cutting tip 9 is set to 0 at the beginning of the drilling procedure, e.g. when the cutting tip 9 of the drill bit 5 is flush with the front end 10 of the displaceable second member 4.

The velocity of the drill bit 5 moving along the x-axis 8 at any instant equals the rate of change of the x versus time graph at that instant and therefore is determined by the first derivative of x with respect to time at that instant. Furthermore, the instantaneous acceleration of the drill bit 5 at any time is the rate of change of the velocity versus time curve at that time and is determined as the second derivative of x with respect to time at that instant. The acceleration peak might occur too late with respect to the point where the cutting tip 9 of the drill bit 5 exits, e.g. the far cortex of the bone. The highest change in acceleration, i.e. the jerk peak occurs closer to the point where the cutting tip 9 of the drill bit 5 exits, e.g. the far cortex of the bone. To permit a more significant identification of the point where the cutting tip 9 of the drill bit 5 exits, e.g. the far cortex of the bone the jerk of the drill bit 5 is determined. Furthermore, the jerk peak allows to apply a simple peak detector. As defined in physics the jerk is the rate of change of acceleration, that is the derivative of acceleration with respect to time, i.e. the second derivative of velocity and the third derivative of x with respect to time at any instant.

For this purpose the position x or x coordinate of the cutting tip 9 of the drill bit 5 with respect to time is recorded by the processing unit 14 which is integrated in the first member 3 of the measuring device 1.

Exemplarily, but not limiting, the processing unit 14 is configured as a digital processing unit and comprises a microprocessor having a processor register to record the position of the second member 4 relative to the first member 3. As described above the position of the second member 4 relative to the first member 3 coincides with the position x or x coordinate of the cutting tip 9 of the drill bit 5 relative to the front end 10 of the displaceable second member 4. Furthermore, the microprocessor is suitably programmed for a numerical differentiation of digitized signals, i.e. to compute the at least first and second derivatives of the position x or x coordinate with respect to time and is further programmed to detect acceleration and/or jerk peaks on the basis of the acceleration and/or jerk acting on the drill bit 5 and determined via the differentiators.

Alternatively, as mentioned above the processing unit 14 can be configured by using analog technique, e.g. electronic circuits including one or more electronic circuits acting as differentiators and an electronic circuit acting as a peak detector.

By means of the one or more differentiators the instantaneous acceleration of the drill bit 5 at any time is determined as the second derivative of x with respect to time at that instant. Additionally, the jerk as the derivative of acceleration with respect to time, i.e. the second derivative of velocity and the third derivative of x with respect to time at any instant is determined.

Figure 5:
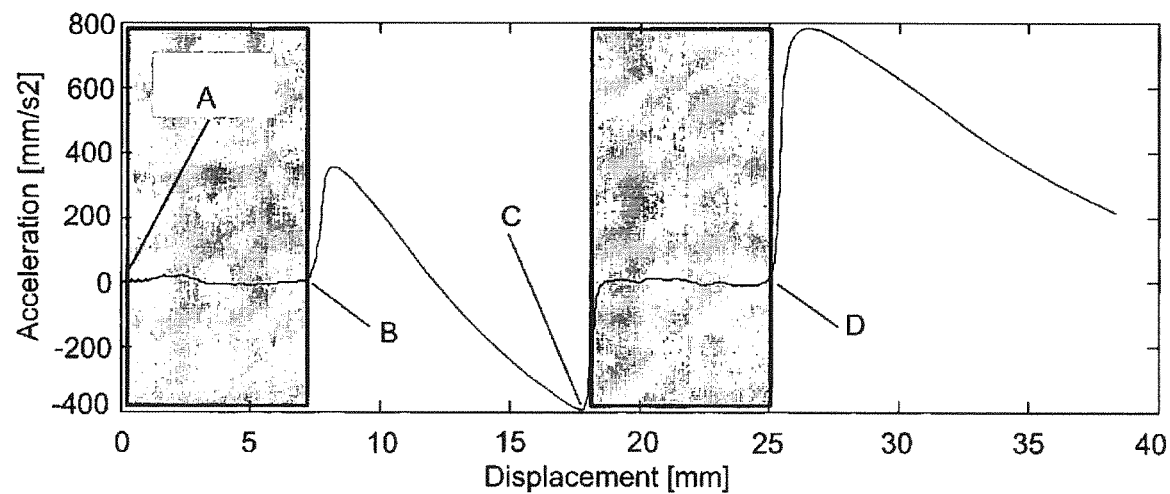
FIG. 5 illustrates a graph of the acceleration of a drill bit versus displacement along the x axis as the line along which the motion takes place.
Figure 6:
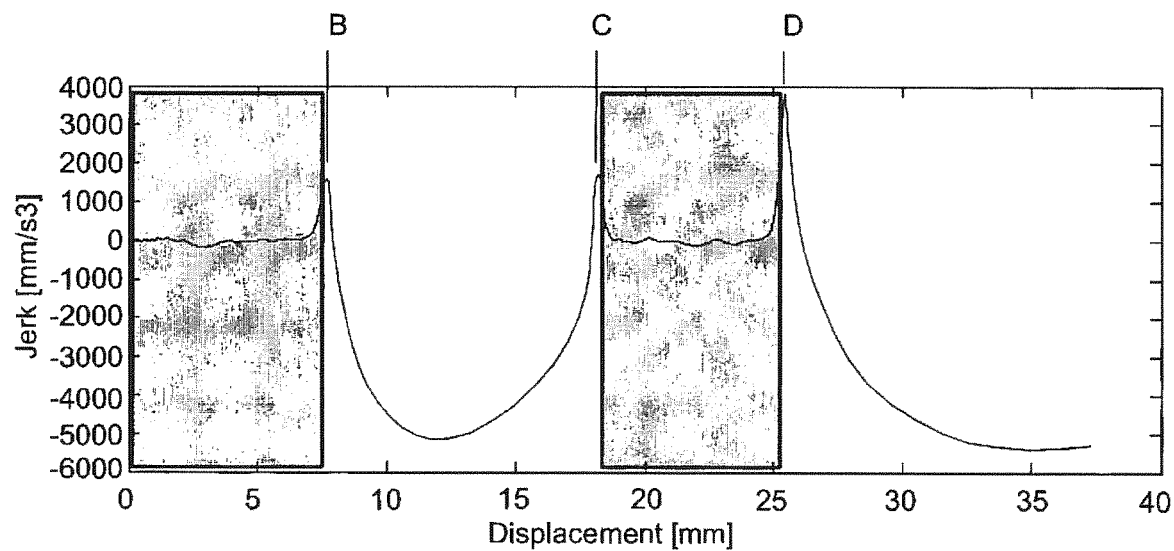
FIG. 6 illustrates a graph of the jerk of the drill bit versus displacement, wherein the jerk is the derivative of the acceleration shown in FIG. 4 with respect to time.

As illustrated in FIG. 5 the acceleration of the drill bit 5 has a first peak when the cutting tip 9 of the drill bit 5 exits the near cortex of a bone (B) and a second peak of the acceleration occurs when the cutting tip 9 of the drill bit 5 exits the far cortex of the bone (D). Furthermore, a sudden increase of the acceleration of the drill bit 5 along the x-axis 8 occurs when the cutting tip 9 of the drill bit 5 enters the far cortex of the bone (C), which however is not followed by a regression so that at this point no acceleration peak appears. FIG. 6 illustrates the jerk acting on the drill bit 5 and being the derivative of acceleration with respect to time. The first peak of the jerk specifies the slope of the tangent of the acceleration versus time graph at that instant, i.e. approximately at the point where the cutting tip 9 of the drill bit 5 exits the near cortex (B), the second peak specifies the slope of the tangent of the acceleration versus time graph at that instant, i.e. at the point where the cutting tip 9 of the drill bit 5 enters the far cortex (C) and the third peak specifies the slope of the tangent of the acceleration versus time graph at that instant, i.e. approximately at the point where the cutting tip 9 of the drill bit 5 exits the far cortex (D).

The data processing effected by the peak detector can include a determination of their positions, heights, and widths. Furthermore, the peak detector can use an amplitude threshold or a slope threshold to reliably identify a peak. Other parameters can be the width of the peak or the area covered by the peak.

In the case the peak detector is configured to use an amplitude threshold so as to identify an acceleration peak when the maximum value of the determined acceleration exceeds a pre-defined threshold value. Particular threshold values can be stored in a data memory electronically connected to the microprocessor and/or temporarily stored in the processor register of the microprocessor.

In the case the peak detector is configured to use a slope threshold, i.e. the jerk for peak identification the processing unit 14 additionally comprises a third differentiator to determine or compute the third derivative of the position x or x coordinate of the cutting tip 9 of the drill bit 5 with respect to time at any instant, wherein the position x or x coordinate coincides again with the displacement of the second member 4 relative to the first member 3. The peak detector is then configured or programmed to identify a jerk peak when the maximum value of the determined jerk exceeds a pre-defined threshold value for the jerk.

The drill distance to the exit from the second cortex, i.e. the position x or x coordinate of the cutting tip 9 of the drill bit 5 when the cutting tip 9 exits the far cortex is automatically computed based on acceleration and/or jerk peaks. Based on this position x or x coordinate the required screw length, preferably including a safety margin can be estimated. For this purpose the processing unit 14 can comprise a data memory to store data related to bone screw lengths, preferably including safety margin.

The measuring device 1 and particularly the displacement transducers can be either integrated in the housing 12 or can be temporarily attachable thereto. In a temporarily attachable configuration the measuring device 1 comprises attachment means in the form of an adaptor 15 which is releasably affixable to the housing 12 of the surgical power drill 2. This adaptor 15 is exemplarily but not limiting configured as an annular framework attachable to the housing 12 by means of a press fit or via a clamp collar. Alternatively, the measuring device 1 can comprise clamps to releasably affix the measuring device 1 to the housing 12.

The measuring device 1 can comprise a wireless communication device, exemplarily configured as a Bluetooth module 17 with signal conditioner. Via the wireless communication device the data may be transmitted wirelessly to an external computer with monitor, a tablet computer, a smartphone, a smartwatch or a smart glass to compute or indicate the derived information, i.e. the measured position of the cutting tip of the drill bit with respect to time as well as the computed velocity with respect to time, the computed acceleration with respect to time and the computed jerk with respect to time. Alternatively, the derived data may be provided on a display or speaker locally mounted to the surgical power drill 2.

Additionally, the measuring device 1 comprises a sterilizable casing 16 to enclose the processing unit 14, the wireless communication device and the power supply 22 for the measuring device 1, wherein the power supply 22 includes one or more rechargeable or non-rechargeable batteries arrangeable in the casing 16.

Figure 7:
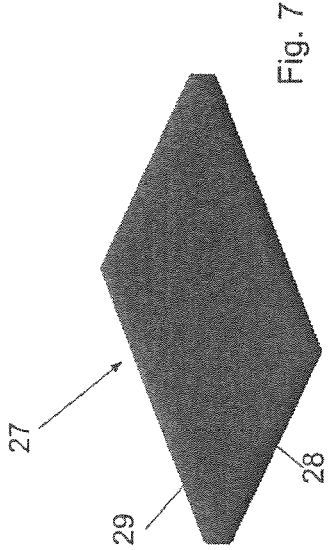
FIG. 7 illustrates a perspective view of a calibration device for use with the device according to the invention.
Figure 8:
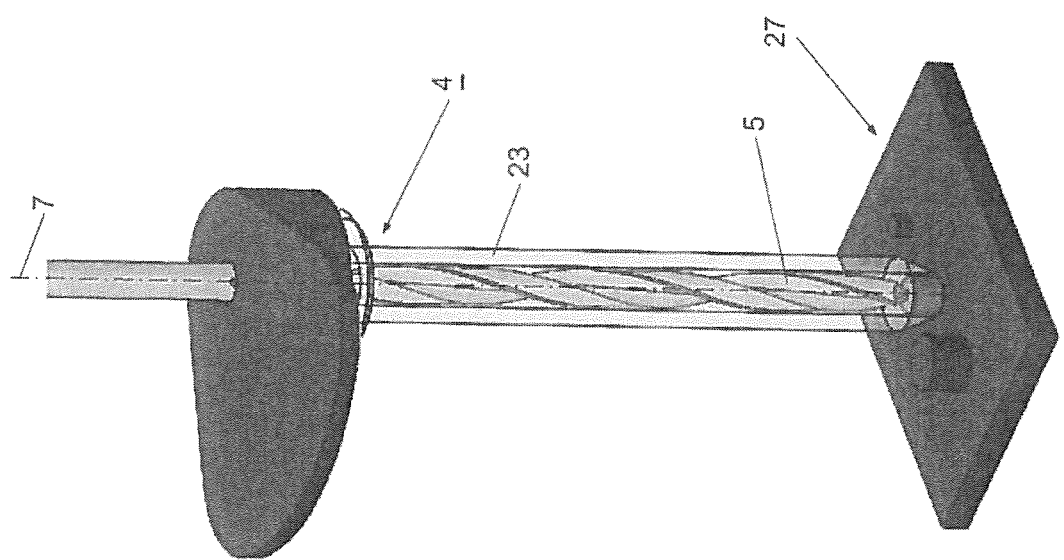
FIG. 8 illustrates a perspective view of the calibration device of FIG. 7 together with a drill bit and an embodiment of the displaceable second member of the device according to the invention.

Furthermore, the device 25 can additionally comprise a calibration device 27 as illustrated in FIGS. 7 and 8 and described in more detail below.

Figure 2:
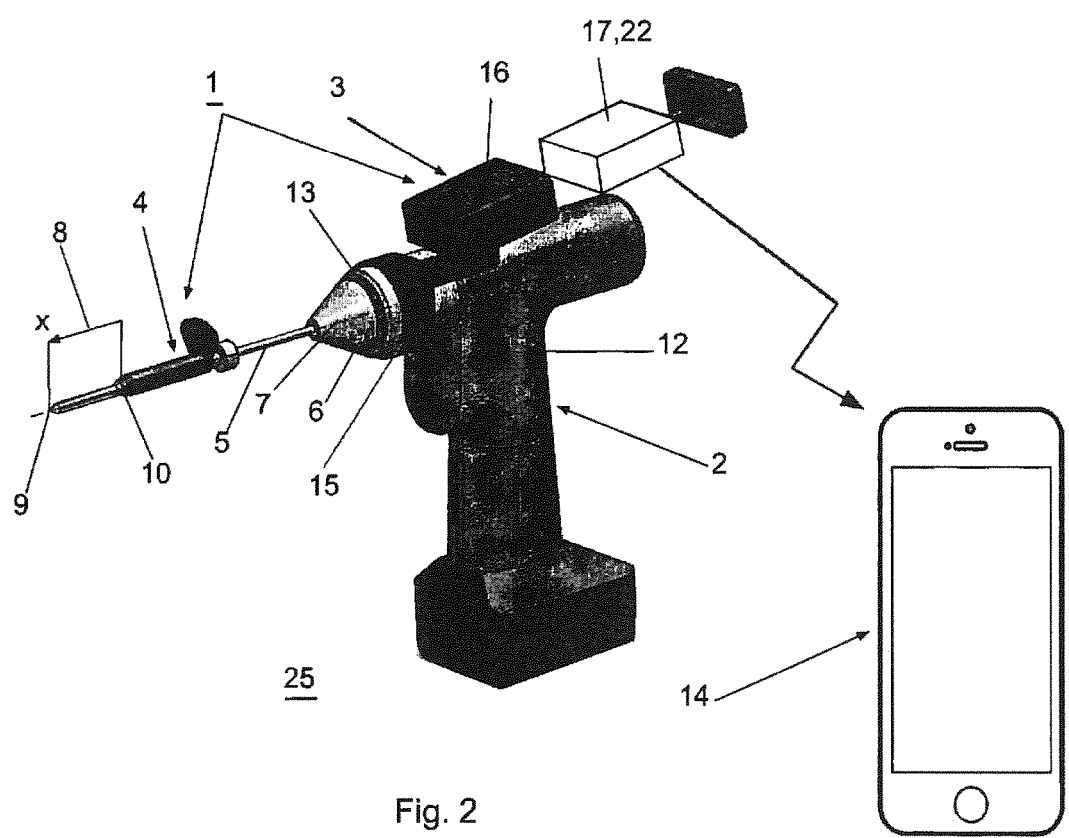
FIG. 2 illustrates a perspective view of another embodiment of the device according to the invention.

Another embodiment of the device 25 according to the invention is illustrated in FIG. 2, wherein the device 25 of FIG. 2 differs from the embodiment of FIG. 1 only therein that the processing unit 14 is an external unit, e.g. a computer with monitor, a tablet computer, a smartphone, a smartwatch or a smartglass, and that the measuring device 1 comprises a wireless data transmission device 17 and the processing unit 14 includes a wireless data receiving device so that the measured distance x covered by the housing 12 in the direction of the longitudinal axis 7 and relative to a surface of an implant 26 or a bone can be transmitted from the measuring device 1 to the external processing unit 14 and recorded with respect to time. The external processing unit 14 can comprise a microprocessor similar to the embodiment of FIG. 1 or can comprise a central processing unit.

Figure 3:
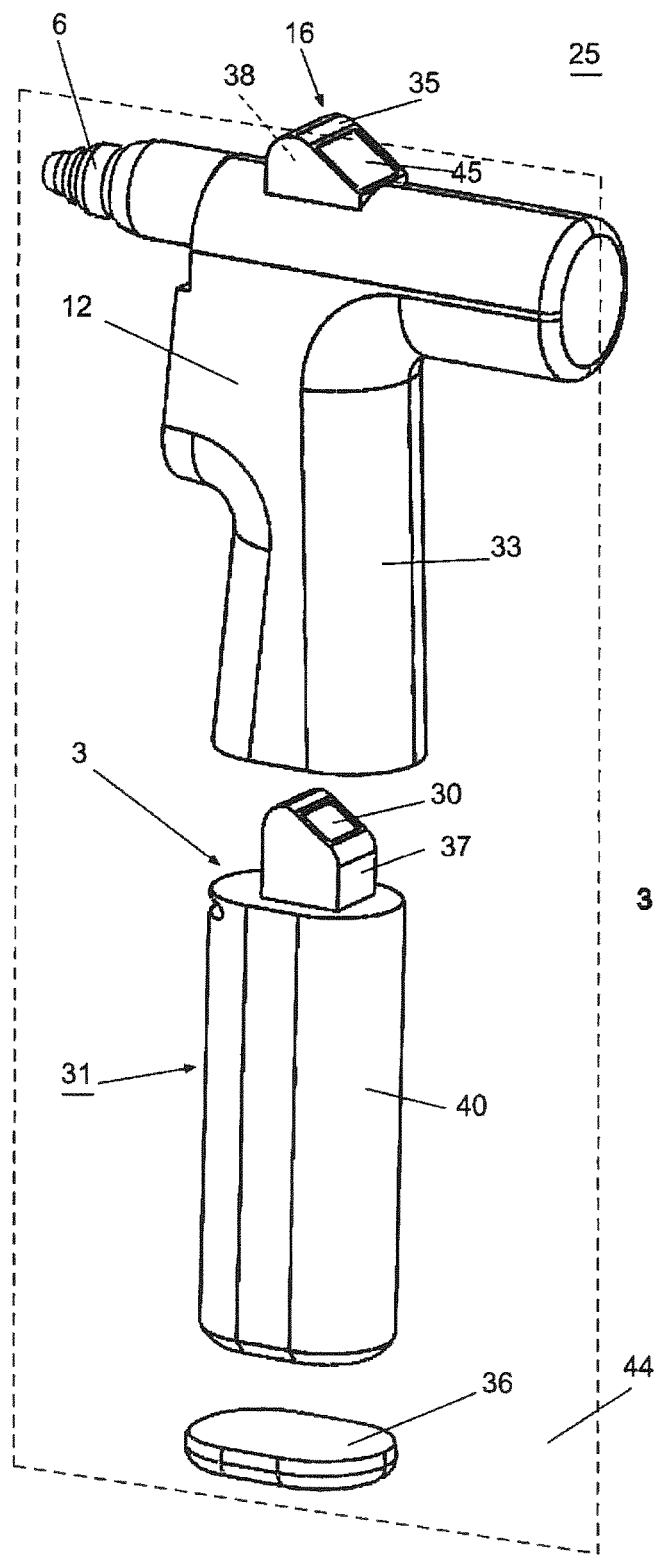
FIG. 3 illustrates a perspective view of a further embodiment of the device according to the invention.
Figure 4:
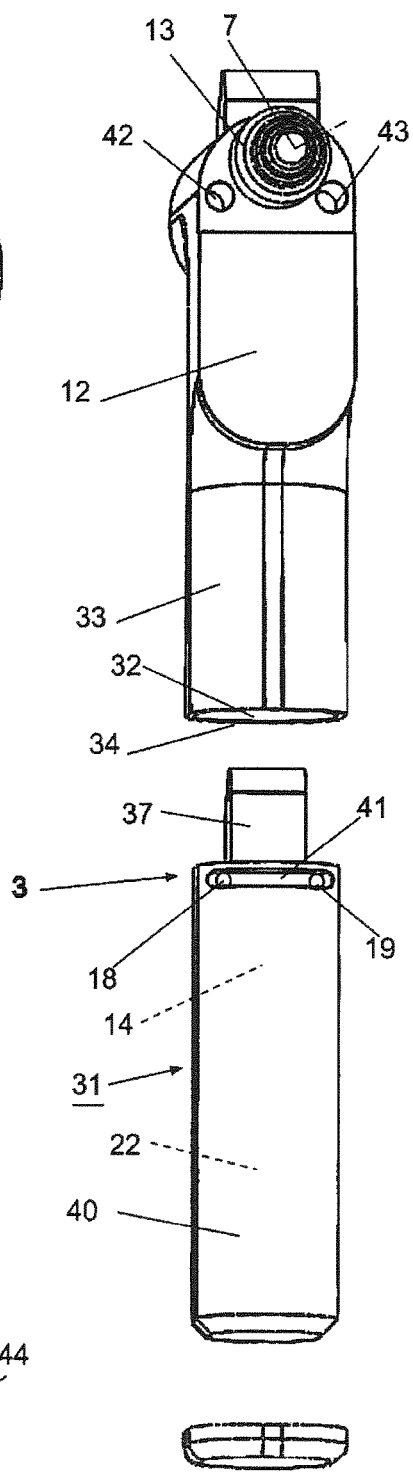
FIG. 4 illustrates an exploded front view of the embodiment of FIG. 3.

A further embodiment of the device 25 according to the invention is illustrated in FIGS. 3 and 4, wherein the measuring device 1 of the embodiment of FIGS. 3 and 4 differs from the embodiment of FIG. 1 therein that the first member 3 including the laser module 18 for emitting a laser beam and the receiver for triangulation, e.g. an electronic light sensor 19 in the form of a photodiode or a charge-coupled device (CCD) is configured as a part of an electronic module 31. This electronic module 31 is insertable into a hollow space 32 formed in the handle 33 of the housing 12, wherein the hollow space 32 extends from an opening 34 at the bottom of the handle 33 to the top part 35 of the housing 12. The opening 34 can be closed by means of a cover 36 which is attachable to the bottom of the handle 33.

Apart from the first member 3 the electronic module 31 comprises a display 30 which is arranged in an upper part 37 of the electronic module 31, wherein this upper part 37 is shaped and dimensioned to fit into a respective cavity 38 configured in the top part 35 of the housing 12. Furthermore, the electronic module 31 has a lower part 40 including the laser module 18, the electronic light sensor 19, the processing unit 14 and a power supply 22 for driving the surgical power drill 2 and for supplying the laser module 18, the light sensor 19 and the processing unit 14. Exemplarily, the power supply 22 can be a battery or an accumulator. The lower part 40 of the electronic module 31 is shaped and dimensioned to fit into the hollow space 32 in the handle 33 of the housing 12. A laser window 41 is arranged at the front of the lower part 40 and just below the upper part 37 of the electronic module 31 so as to match the laser beam and the electronic light sensor 19 with respective windows 42, 43 (FIG. 4) in the housing 12.

A first and a second sterile window 42, 43 are arranged in the housing 12 of the surgical power drill 2 to provide windows for the laser beam emitted by the laser module 18 and the reflected beam received by the electronic light sensor 19. The first and second sterile windows 42, 43 are arranged in the front of the housing 12 and—when viewed in a front view—below the longitudinal axis 7 of the spindle 13 and located on opposite sides of a middle plane 44 of the surgical power drill 2 which contains the longitudinal axis 7 and at a distance from the middle plane 44 which permits the laser beam and the reflected beam to pass beside the spindle 13 and the chuck 6 of the surgical power drill 2.

The top part 35 of the housing 12 forms a casing 16 for the display 30, wherein the casing 16 is, exemplarily but not limiting, integral with the housing 12 of the surgical power drill 2 and encompasses the cavity 38. This casing 16 comprises a third sterile window 45 for covering the display 30. Further the casing 16 is arranged at the housing 12 opposite the handle 33 of the surgical power drill 2. The third sterile window 45 is angled relative to a plane orthogonal to the longitudinal axis 7 of the spindle 13 and directed towards the rear end of the housing 12.

Exemplarily but not limiting the measuring device 1 is suitably configured to control the rotational speed of the spindle 13 of the surgical power drill 2 so that the power supplied to the electric motor of the power drill 2 can be shut down when a peak is detected by means of the measuring device 1 to thereby prevent plunging of the drill bit 5.

Again another embodiment of the device 25 according to the invention is illustrated in FIGS. 12-15, wherein the measuring device 1 of the embodiment of FIGS. 12-15 differs from the embodiment of FIG. 1 therein that the first member 3 includes an electronic module 31 which comprises apart from the laser module 18 for emitting a laser beam and the receiver for triangulation, e.g. an electronic light sensor 19 in the form of a photodiode or a charge-coupled device (CCD) a display 30. Further the electronic module 31 comprises the processing unit 14 and the power supply 22 for the measuring device 1. The display 30 is arranged at the rear side 46 of the electronic module 31. Similarly to the embodiment of FIG. 1 the sterilizable casing 16 is attachable to the surgical power drill 2 and comprises a cavity 38 to receive the electronic module 31. A sterile front window 47 is arranged in the front of the casing 16 to let through the laser beam emitted by the laser module 18 and the reflected beam reflected by means of the reflector 20 arranged at the second member 4 of the measuring device 1.

The laser module 18 and the electronic light sensor 19 which receives the reflected beam to perform the triangulation are arranged laterally spaced from each other in the electronic module 31 so that—when viewed in a front view of the assembled first member 3—the laser beam and the reflected beam pass above the longitudinal axis 7 of the spindle 13.

The casing 16 comprises an adaptor 15 to secure the first member 3 of the measuring device 1 to the housing 12, wherein the adaptor 15 is releasably affixable to the housing 12 of the surgical power drill 2. This adaptor 15 is, exemplarily but not limiting, configured as an annular framework attachable to the housing 12 by means of a clamp collar 48 that is fixable, e.g. to the stationary part of the spindle 13 by means of a clamping screw 49.

The clamp collar 48 is positioned at the casing 16 laterally offset with respect to a longitudinal central plane of the casing 16 to permit the laser beam and the reflected beam to pass beside the drill bit 5. Furthermore, by means of the adaptor 15 the casing 16 is attached to the surgical power drill 2 at an angle with respect to the longitudinal axis 7 so that the laser beam is emitted at an angle to the longitudinal axis 7 permitting a reduced size of the reflector 20 of the second member 4 of the measuring device 1.

The casing 16 is sterilizable and configured as a separate piece arranged on top of the housing 10. The cavity 38 has an opening at the rear side of the casing 16 and can be closed by means of a lid 51 which is rotatable about an axis located at the lower side of the casing 16 and extending orthogonally to the longitudinal axis. The lid 51 comprises a sterile rear window 52 for covering the display 30, wherein—when the lid 51 is closed—the rear window 52 is angled relative to a plane orthogonal to the longitudinal axis 7 of the spindle 13 and directed towards the rear end of the housing 12.

Exemplarily but not limiting, an actuator 53 for a power switch of the electronic module 31 can be arranged at the inside of the lid 51 so that when the lid 51 is closed energy is supplied from the power supply 22 to the electronic components of the measuring device 1. To operate the processing unit 14, the laser module 18 and the electronic light sensor 19 one or more buttons 54 can be positioned at the rear side of the electronic module 31. The sterile rear window 52 can be provided with recesses so as to provide weakened areas in the rear window 52 which permit to actuate the one or more buttons 54 when the lid 51 is in its closed position.

The processing unit 14 of the embodiments of FIGS. 1-4 and 12-15 comprises a microprocessor or a central processing unit which includes a processor register to record the distance x covered by the housing 12 in the direction of the longitudinal axis 7 and relative to a surface of an implant 26 or a bone with respect to time during a drilling process. Furthermore, the processor register of the microprocessor or central processing unit temporarily stores acceleration and/or jerk peak values determined during a drilling process to define threshold values for acceleration and/or jerk. By this means the threshold values can be retrospectively set in relation to the maximum recorded peak under the assumption that the number of expected peaks is known (e.g. two peaks for the near and far cortex).

Furthermore, the microprocessor or central processing unit of the processing unit 14 of the embodiments of FIGS. 1-4 and 12-15 can be programmed to compute the derivatives, to detect the peaks and to output the current distance x, the current velocity and the position x of the cutting tip 9 of the drill bit 5 at the most recent jerk peak in real-time. As described above the numerical differentiation requires at least two or three adjacent data points $x_{i-1}$ ($t_{i-1}$), $x_i$ ($t_i$) and $x_{i+1}$ ($t_{i+1}$). Therefore, for real-time processing of the derivatives and the peak detection the processing unit 14 temporarily stores or records at least two or more adjacent data points.

Alternatively, the microprocessor or central processing unit of the processing unit 14 of the embodiments of FIGS. 1-4 and 12-15 can be programmed for retrospective data processing, so as to first record the complete set of data points x with respect to time during the whole drilling process and to compute the derivatives and perform the peak detection once the drilling procedure has been completed.

It has to be noted that real-time feedback of current drill depth alone can be of high value for the surgeon. Further valuable information is delivered by the current drilling speed. This helps the surgeon to control his feed rate to avoid mechanical or heat damage of the bone or it can be used to estimate the bone quality.

Figure 16:
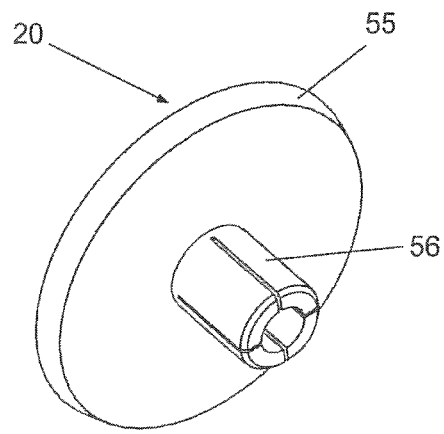
FIG. 16 illustrates a perspective view of a displaceable second member of the measuring device according to another embodiment of the device according to the invention.

FIG. 16 illustrates another embodiment of the reflector 20 which is not integral with or attached to a drill sleeve 23. The reflector 20 is clampable onto the drill bit 5 in such a way that it can slide on the drill bit 5 so that the reflector 20 is independent from the configuration of the drill sleeve 23. The reflector 20 has a disc shaped portion 55 and adjoining thereto a clamping portion 56 comprising longitudinal slots so as to form tongues suitable to exert radial pressure onto the drill bit 5.

Figure 18:
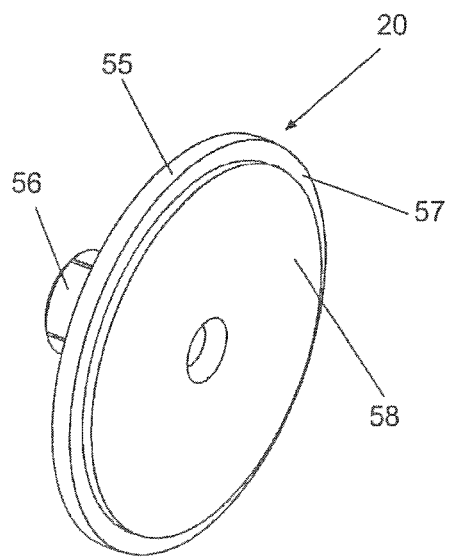
FIG. 18 illustrates a perspective view of a displaceable second member of the measuring device according to a further embodiment of the device according to the invention.

FIG. 18 illustrates again another embodiment of the reflector 20 which differs from the embodiment of FIG. 16 only therein that the reflector 20 has a reflecting surface 58 facing away from the clamping portion 56, wherein the reflecting surface 58 includes a groove 57 extending along the periphery of the disc shaped portion 55. Exemplarily, the event when laser spot produced by the laser beam on the rear side of the disc shaped portion 55 jumps into the groove 57 can be used as a switch or trigger for actions, e.g. to stop the rotation of the spindle 13 and the depth or position of groove 57 can be used to select e.g. the screw module, e.g. 5 mm or 3.5 mm or 2.4 mm.

The method for bone screw length estimation from drilling characteristics essentially comprises the steps: A) advancing the surgical power drill 2 coaxially to the longitudinal axis 7 of the spindle 13 to drill a hole in a bone and by recording the position x of the cutting tip 9 of the drill bit 5 with respect to time; B) determining the first, second and third derivative of x versus t at any instant; C) determining the instant when the cutting tip 9 of the drill bit 5 exits a cortex of a bone by using the peak detector to identify a jerk peak occurring at that instant, wherein the graphs of velocity, acceleration and jerk versus time are derived via the derivatives at any instant determined under step B). False solutions are excluded by analyzing the signs of the velocity and acceleration signals at the instant. In order to determine whether the identified jerk peak relates to deceleration (entering bone) or acceleration (exiting bone) the sign of the acceleration at the instant is consulted. By additionally consulting the sign of the velocity at the instant, it is ensured to only consider peaks occurring while advancing the drillbit as opposed to retracting it; D) determining the relative position between the second member 4 and the first member 3 at the instant determined under step C); and E) selecting a bone screw having a length corresponding to the relative position between the second member 4 and the first member 3 determined under step D) under consideration of a predefined safety margin.

As described above the position x of the cutting tip 9 of the drill bit 5 relative to a surface of a bone or of an implant 26 in the drilling direction is set to zero at the beginning of the drilling process. However, this zero position of the cutting tip 9 of the drill bit 5 depends on the fact whether:
1) the displaceable second member 4 comprises a drill sleeve 23 extending in the direction of the longitudinal axis 7 to the front end 10 of the second member 4 as illustrated in FIGS. 3, 4 and 11a-11e; or whether
2) the drill sleeve is a separate member previously inserted in the soft tissue covering the bone to be treated; or whether
3) the zero position of the cutting tip 9 is to be set with respect to an implant 26, e.g. a bone plate. In case the drill bit 5 is guided in a drill sleeve 23 which during drilling contacts or attaches to a bone plate and hence doesn't allow the cutting tip 9 of the drill bit 5 to abut the upper surface of the bone plate (FIG. 9) a calibration device 27 providing a physical stop 28 inside the drill sleeve 23 at a height corresponding with the upper surface of the bone plate can be used to determine the start point of the measurement (FIG. 8). Alternatively, if the lengths of drill bit 5 and drill sleeve 23 are known, the start point can be computed from this data.

In the case of the above variant 1) the method comprises before step A) the following steps:
positioning the surgical power drill 2 relative to a bone so that the front end 10 of the displaceable second member 4 and the cutting tip 9 of the drill bit 5 abut a surface of a bone; and
storing the relative position as start point (x=0) for the measurement of the position x of the cutting tip 9 of the drill bit 5 relative to a surface of a bone in the drilling direction with respect to time.

In the case of the above variant 2) the method comprises before step A) the following steps:
positioning the surgical power drill 2 relative to a bone so that the front end 10 of the displaceable second member 4 abuts a drill sleeve 23 inserted in the soft tissue covering a bone to be treated; and
adjusting the cutting tip 9 of the drill bit 5 secured in the chuck 6 of the surgical power drill 2 relative to the displaceable second member 4 so that the cutting tip 9 of the drill bit 5 abuts a surface of a bone; and
storing the relative position as start point (x=0) for the measurement of the position x of the cutting tip 9 of the drill bit 5 relative to a surface of a bone in the drilling direction with respect to time.

Figure 10:
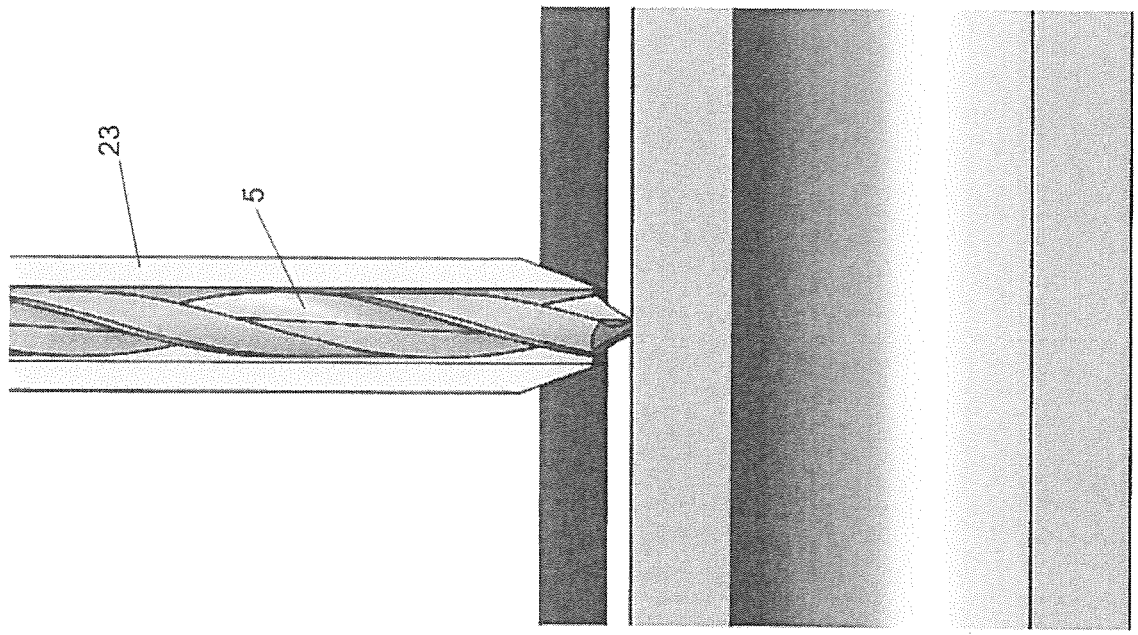
FIG. 10 illustrates a schematic sectional view of an implant positioned on a bone together with a drill bit and an embodiment of the displaceable member of the device according to the invention at the point where the drill bit abuts on the surface of a bone.
Figure 9:
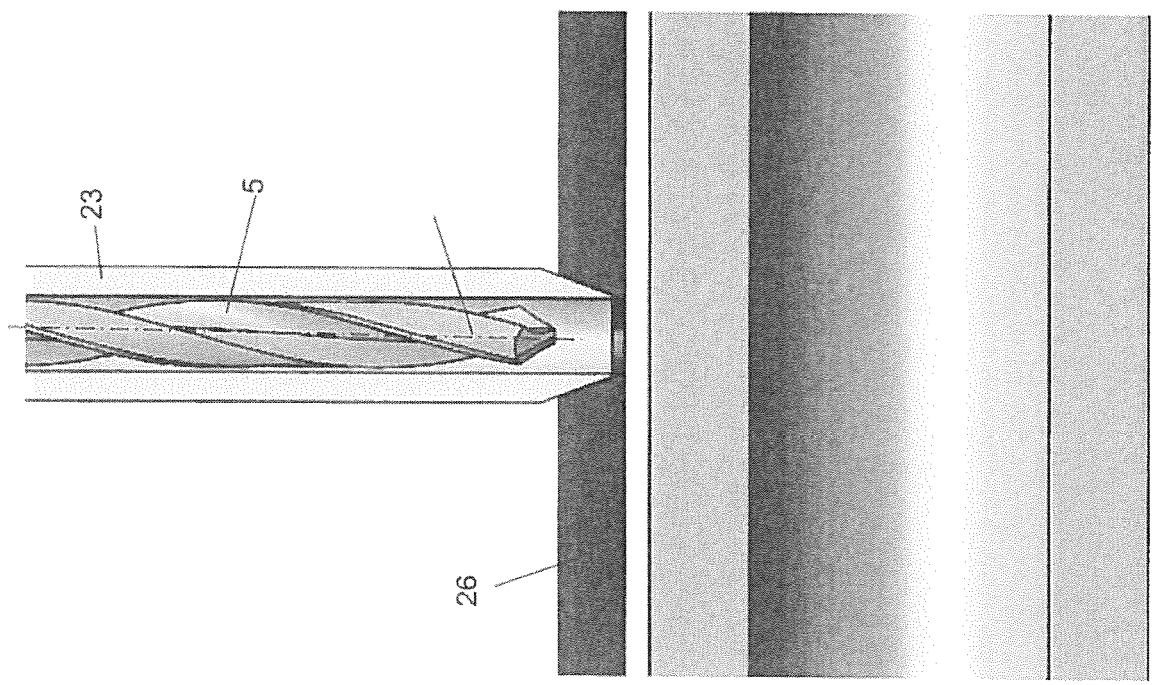
FIG. 9 illustrates a schematic sectional view of an implant positioned on a bone together with a drill bit and an embodiment of the displaceable member of the device according to the invention at the start point of the drilling process.
Figure 11A:
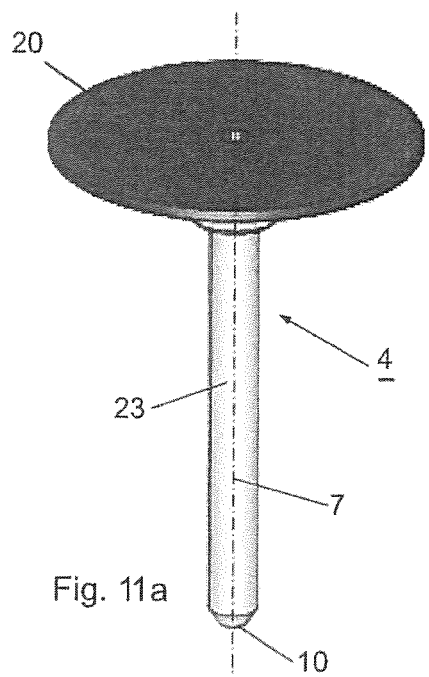
FIGS. 11a-11e illustrate perspective views of different embodiments of the displaceable second member of the device according to the invention.
Figure 11B:
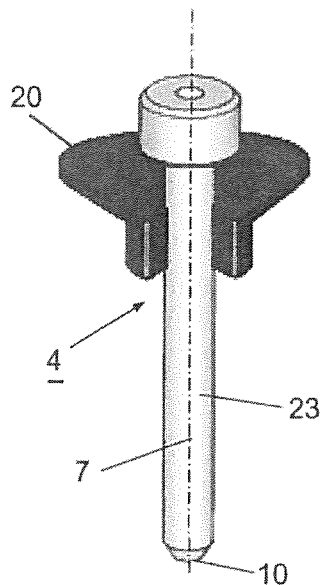
Figure 11C:
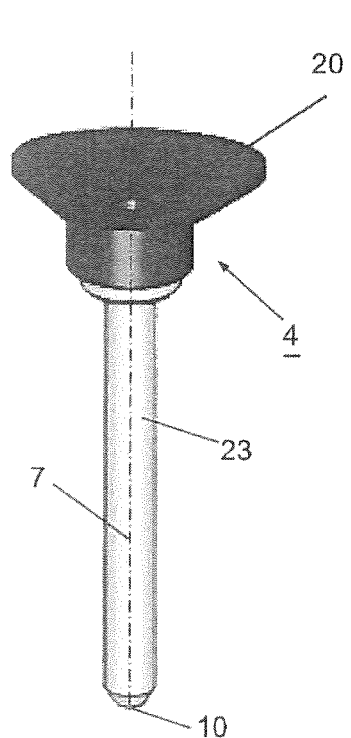
Figure 11D:
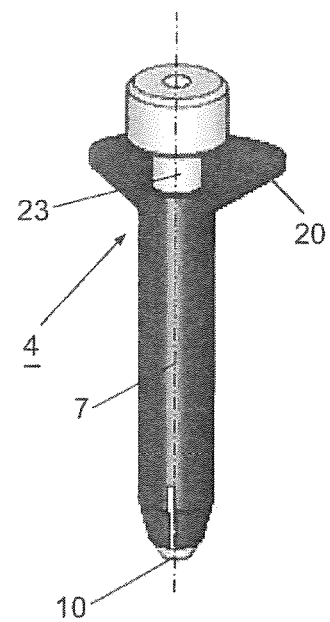
Figure 11E:
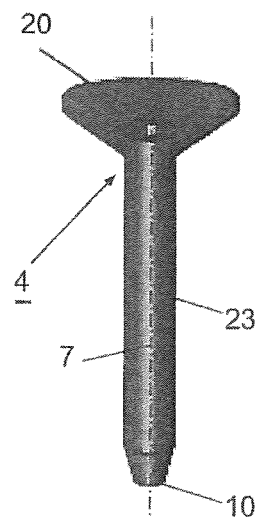
Figure 12:
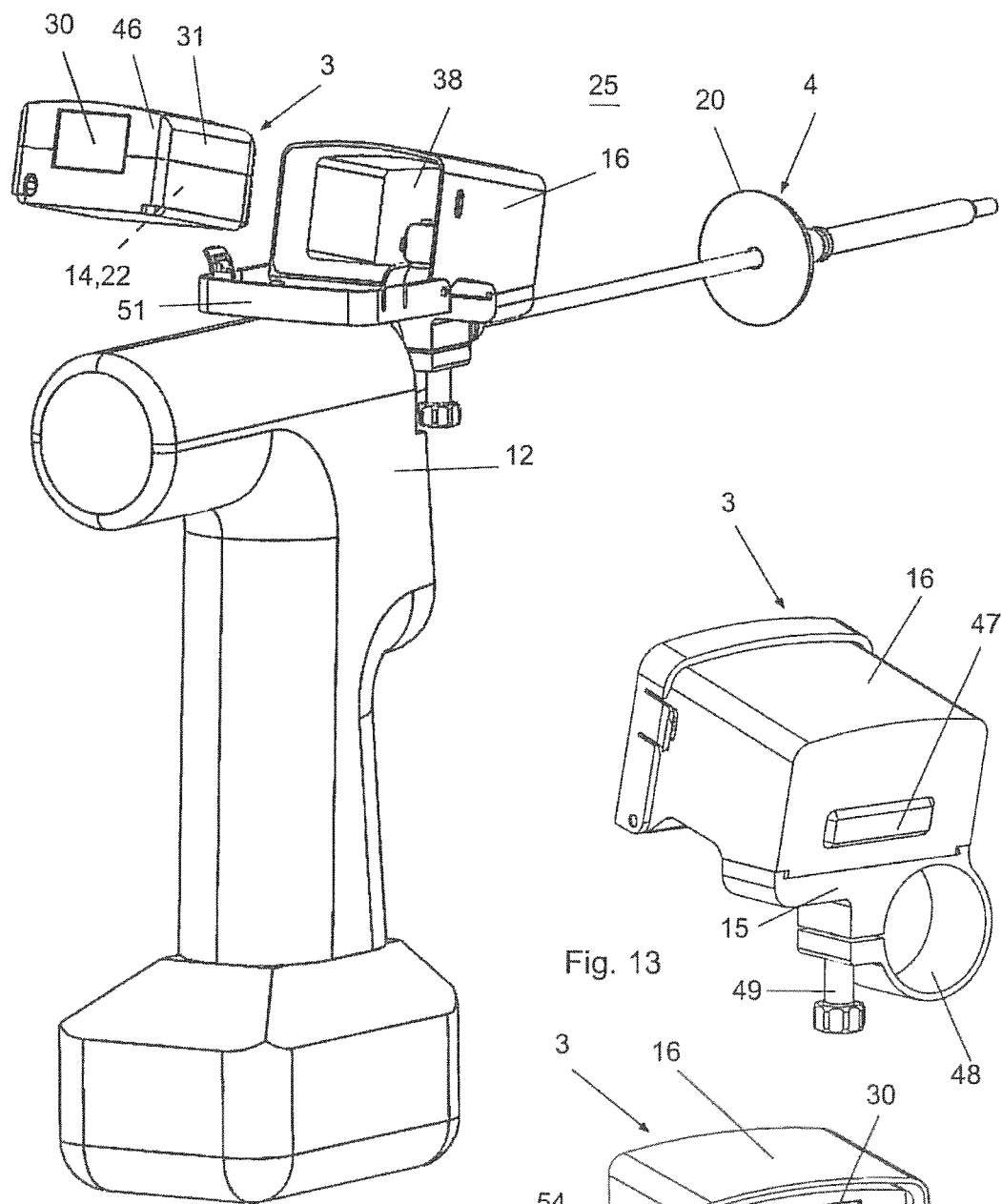
FIG. 12 illustrates a perspective view of another embodiment of the device according to the invention.
Figure 13:
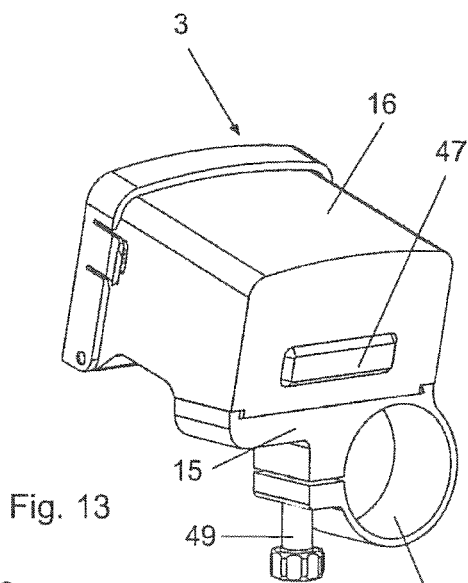
FIG. 13 illustrates a perspective view of the first member of the measuring device of the embodiment of the device according to FIG. 12.
Figure 14:
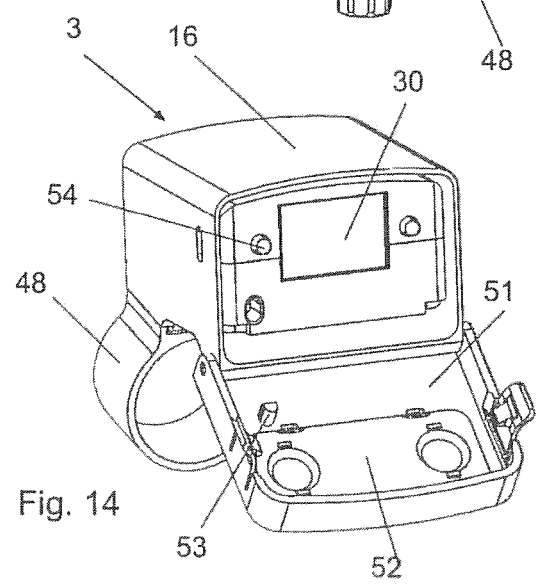
FIG. 14 illustrates another perspective view of the first member of the measuring device of the embodiment of the device according to FIG. 12.
Figure 15:
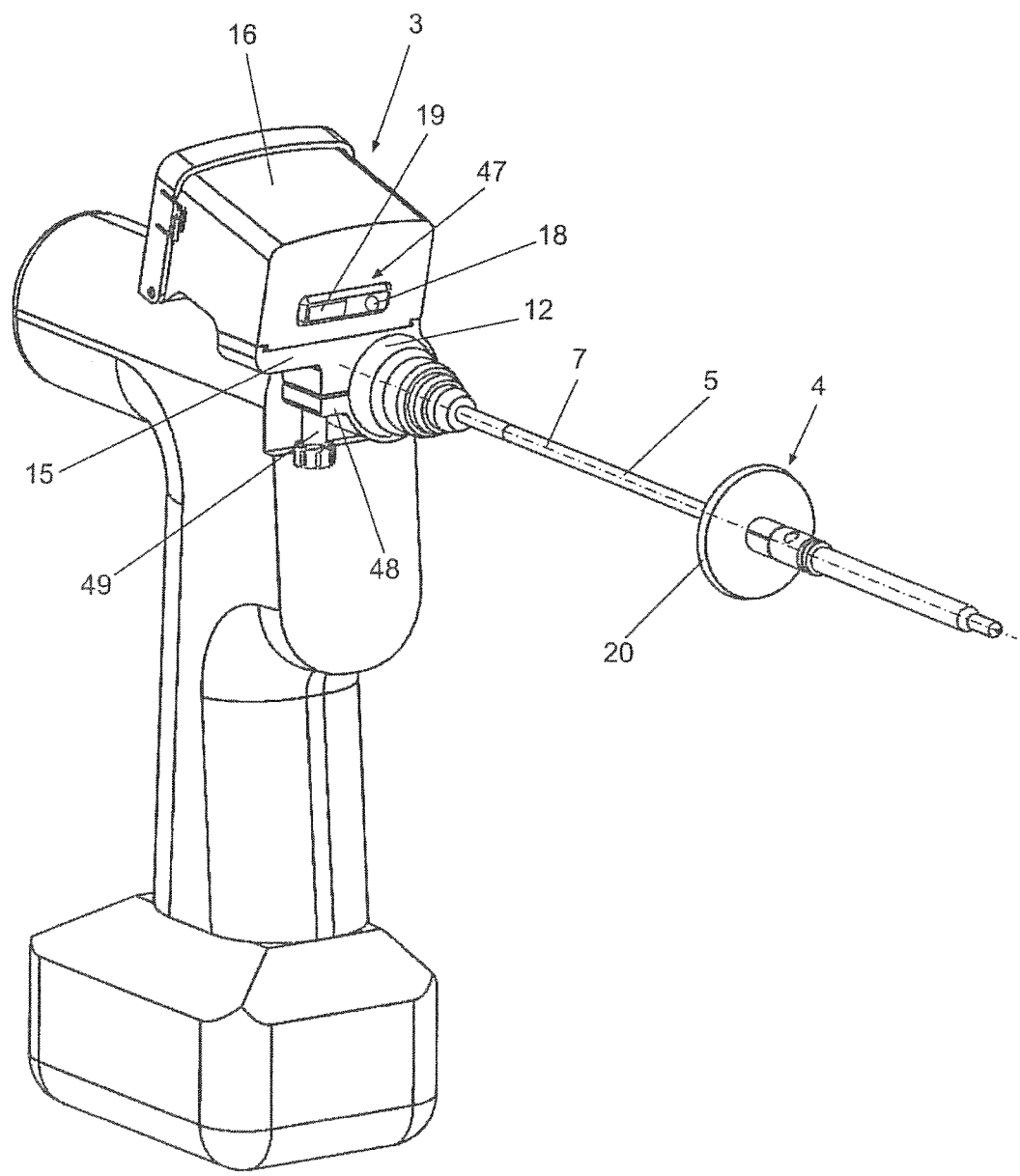
FIG. 15 illustrates perspective view from the front of the embodiment of the device according to FIG. 12.

In the case of the above variant 3) the method comprises before step A) the following steps (FIGS. 9 and 10):
positioning the drill bit 5 secured in the chuck 6 relative to the displaceable second member 4 by using a calibration device 27 (FIGS. 7 and 8) so that front end 10 of the second member 4 contacts a surface 29 of the calibration device 27 and the cutting tip 9 of the drill bit 5 abuts a stop 28 protruding from the surface 29 of the calibration device 27;
storing the relative position as start point (x=0) for the measurement of the position x of the cutting tip 9 of the drill bit 5 relative to a surface of a bone or of an implant 26 in the drilling direction with respect to time; and
positioning the surgical power drill 2 relative to an implant 26, e.g. a bone plate, so that the front end 10 of the displaceable second member 4 abuts a surface of the implant 26 (FIG. 9).

Figure 17:
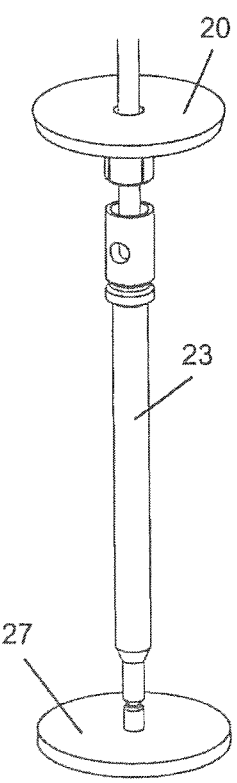
FIG. 17 illustrates a perspective view of an assembly including the displaceable second member of the measuring device according to FIG. 16 together with a drill sleeve and a calibration device.

FIG. 17 illustrates a further embodiment of the calibration device 27. The reflector 20 as e.g. illustrated in FIG. 16 or 17 as well as the calibration device 27, e.g. illustrated in FIGS. 7 and 8 can be made for single use. In other embodiments the drill sleeve 23 according to one of the embodiments illustrated in FIGS. 11a-11e, 16 and 17 can be configured as a disposable member as well and can for this purpose be connected to the calibration device 27 via a predetermined breaking point.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:
1. A device for drilling holes in bone and determining bone screw length, the device comprising:

a surgical power drill comprising:
  a housing in which a motor and a spindle driven by the motor are accommodated, wherein the spindle has a longitudinal axis and comprises a chuck for clamping a drill bit; and
  a measuring device releasably attached to or non-releasably fixed to the housing, wherein the measuring device is configured to measure a distance (x) covered traveled by the housing a direction of the longitudinal axis and relative to a surface of an implant or a bone during a drilling process;
  wherein the measuring device comprises a processing unit configured to record the distance (x) traveled by the housing in the direction of the longitudinal axis and relative to the surface of the implant or the bone with respect to time;
  wherein the processing unit comprises one or more differentiators configured to determine at least first and second derivatives of the distance (x) traveled with respect to time at any instant and to record at least a graph of a highest derivative with respect to time;
  wherein the processing unit further comprises a peak detector configured to analyze one or more peaks occurring in the graph of the highest derivative with respect to time; and
  wherein the measuring device further comprises a laser device or an ultrasound position sensor for displacement assessment.

2. The device according to claim 1, wherein the peak detector is configured to identify an acceleration peak when a maximum value of determined acceleration exceeds a pre-defined threshold value.

3. The device according to claim 1, wherein the peak detector is configured to identify a jerk peak when a maximum value of a determined jerk exceeds a predefined threshold value.

4. The device according to claim 1, wherein the processing unit comprises a microprocessor or a central processing unit having a processor register configured to record the distance (x) traveled by the housing in the direction of the longitudinal axis and relative to the surface of the implant or the bone with respect to time during the drilling process, wherein the microprocessor or central processing unit is programmed to compute the at least first and second derivatives of the distance (x) traveled by the housing in the direction of the longitudinal axis and relative to the surface of the implant or the bone with respect to time and thus forms at least a first and a second differentiator and wherein the microprocessor or central processing unit is programmed to form the peak detector.

5. The device according to claim 4, wherein the processor register of the microprocessor or central processing unit temporarily stores acceleration and/or jerk peak values determined during the drilling process to define threshold values for acceleration and/or jerk.

6. The device according to claim 4, wherein the microprocessor or central processing unit is programmed to compute the derivatives, to detect the peaks and to output a current distance (x) and/or a current velocity in real-time.

7. The device according to claim 1, wherein the measuring device comprises an adaptor which is releasably affixable to the housing of the surgical power drill.

8. The device according to claim 1, wherein the measuring device comprises clamps to releasably affix the measuring device to the housing.

9. The device according to claim 1, wherein the measuring device comprises a casing that encloses the processing unit.

10. The device according to claim 1, wherein the laser device comprises a laser module and at least two electronic light sensors configured to perform laser triangulation for displacement assessment.

11. The device according to claim 1, wherein the laser device comprises a reflector that is slideable along the drill bit and configured to abut the implant, the bone or an instrument.

12. The device according to claim 1, wherein the processing unit comprises a data memory configured to store data related to bone screw lengths, screw head length, tip section length and screw length increments.

13. The device according to claim 1, wherein the measuring device further comprises a display or a loud speaker.

14. The device according to claim 1, wherein the device further comprises a calibration device.

15. The device according to claim 1, wherein the measuring device comprises:
  a first member, which is in a fixed position relative to the housing; and
  a longitudinal second member, which is displaceable in the direction of the longitudinal axis of the spindle relative to the first member and which comprises a front end configured to abut the surface of the bone or the implant.

16. The device according to claim 15, wherein the displaceable second member comprises a clamping portion for attachment to cylindrical structures with variable diameters, and wherein the clamping portion of the displaceable second member is configured to provide a frictional fit to the drill bit.

17. A method for estimating bone screw length based on drilling characteristics using a device according to claim 15, said method comprising steps of:
  A) advancing the surgical power drill coaxially to the longitudinal axis of the spindle to drill a hole in a bone and, by recording a position (x) of a cutting tip of the drill bit relative to the surface of the bone or of the implant in a drilling direction with respect to time (t);
  B) determining first, second and third derivatives of x versus t at any instant;
  C) determining an instant when the cutting tip of the drill bit exits a cortex of the bone by using the peak detector to identify a jerk peak occurring at that instant, wherein graphs of velocity, acceleration and jerk versus time are derived via the derivatives at any instant determined under step B);
  D) determining a relative position between the second member and the first member at the instant determined under step C); and
  E) selecting a bone screw having a length corresponding to the relative position between the second member and the first member determined under step D) under consideration of a predefined safety margin.

18. The method according to claim 17, further comprising, before step A), steps of:
  positioning the surgical power drill relative to the bone so that a front end of the displaceable second member and the cutting tip of the drill bit abut the surface of a bone; and
  storing a relative position from the positioning step as a start point (x=0) for measurement of the position (x) of the cutting tip of the drill bit relative to the surface of the bone in the drilling direction with respect to time.

19. The method according to claim 17, further comprising, before step A), steps of:

positioning the surgical power drill relative to the bone so that a front end of the displaceable second member abuts a drill sleeve inserted in soft tissue covering the bone;

adjusting the cutting tip of the drill bit secured in the chuck of the surgical power drill relative to the displaceable second member so that the cutting tip of the drill bit abuts the surface of the bone; and storing a relative position from the positioning step as a start point (x=0) for measurement of the position (x) of the cutting tip of the drill bit relative to the surface of the bone or of the implant in the drilling direction with respect to time.

20. The method according to claim 17, further comprising, before step A), steps of:

positioning the drill bit secured in the chuck relative to the displaceable second member using a calibration device such that a front end of the second member contacts the surface of the calibration device and the cutting tip of the drill bit abuts a stop protruding from the surface of the calibration device;

storing a relative position from the positioning step as a start point (x=0) for measurement of the position (x) of the cutting tip of the drill bit relative to the surface of the bone or of the implant in the drilling direction with respect to time; and positioning the surgical power drill relative to the implant such that the front end of the displaceable second member abuts the surface of the implant.

21. A device for drilling holes in bone and determining a length of a bone screw or a guide wire, the device comprising:

a surgical power drill comprising:

a housing in which a motor and a spindle driven by the motor are accommodated, wherein the spindle has a longitudinal axis and comprises a chuck for clamping a drill bit;

a measuring device releasably attached to or non-releasably fixed to the housing, wherein the measuring device is configured to measure a distance (x) traveled by the housing in a direction of the longitudinal axis and relative to a surface of an implant, instrument or a bone during a drilling process, wherein the measuring device comprises a wireless data transmission device; and a processing unit including a wireless data receiving device, said processing unit being configured to record the distance (x) traveled by the housing in the direction of the longitudinal axis and relative to the surface of the implant, instrument or the bone with respect to time;

wherein the processing unit comprises one or more differentiators configured to determine at least first and second derivatives of the distance (x) covered with respect to time at any instant and to record at least a graph of a highest derivative with respect to time;

wherein the processing unit further comprises a peak detector configured to analyze one or more peaks occurring in the graph of the highest derivative with respect to time; and wherein the measuring device further comprises a laser device or an ultrasound position sensor for displacement assessment.

22. The device according to claim 21, wherein the processing unit is selected from a group consisting of a computer with a monitor, a tablet computer, a smartphone, a smartwatch and a smartglass, wherein the processing unit is programmed to compute at least the first and second derivatives of the distance (x) traveled with respect to time and thus forms at least a first and a second differentiator, and wherein the processing unit is programmed to form the peak detector.

23. The device according to claim 22, wherein the processing unit further comprises a third differentiator configured to determine a third derivative of the distance (x) traveled by the housing in the direction of the longitudinal axis and relative to the surface of the implant or the bone with respect to time during the drilling process.

* * * * *